United States Patent
Piferi et al.

(10) Patent No.: US 9,192,446 B2
(45) Date of Patent: Nov. 24, 2015

(54) TRAJECTORY GUIDE FRAME FOR MRI-GUIDED SURGERIES

(71) Applicant: MRI Interventions, Inc., Memphis, TN (US)

(72) Inventors: Peter Piferi, Orange, CA (US); Daniele Ghidoli, Laguna Hills, CA (US); Rajesh Pandey, Irvine, CA (US); Jesse Flores, Perris, CA (US)

(73) Assignee: MRI Interventions, Inc., Irvine, CA (US)

( * ) Notice: Subject to any disclaimer, the term of this patent is extended or adjusted under 35 U.S.C. 154(b) by 242 days.

(21) Appl. No.: 13/801,190

(22) Filed: Mar. 13, 2013

(65) Prior Publication Data

US 2014/0066750 A1   Mar. 6, 2014

Related U.S. Application Data

(60) Provisional application No. 61/697,090, filed on Sep. 5, 2012.

(51) Int. Cl.
*A61B 19/00* (2006.01)
*A61B 5/055* (2006.01)
(Continued)

(52) U.S. Cl.
CPC ............ *A61B 19/201* (2013.01); *A61B 5/055* (2013.01); *A61B 2017/00911* (2013.01); *A61B 2017/3407* (2013.01); *A61B 2019/5454* (2013.01)

(58) Field of Classification Search
CPC ............... A61B 19/201; A61B 2017/00911; A61B 2017/3407; A61B 5/055; A61B 2019/5454
See application file for complete search history.

(56) References Cited

U.S. PATENT DOCUMENTS

| 4,051,845 A | 10/1977 | Collins |
| 4,209,258 A | 6/1980 | Oakes |

(Continued)

FOREIGN PATENT DOCUMENTS

| DE | 196 25 834 A1 | 1/1998 |
| DE | 10029736 A1 | 3/2002 |

(Continued)

OTHER PUBLICATIONS

International Search Report and Written Opinion Corresponding to International Application No. PCT/US2013/057932; Date of Mailing: Dec. 2, 2013; 12 Pages.

(Continued)

*Primary Examiner* — Long V Le
*Assistant Examiner* — Colin T Sakamoto
(74) *Attorney, Agent, or Firm* — Myers Bigel Sibley & Sajovec, PA

(57) ABSTRACT

An MRI-guided interventional system for use with a patient and an interventional device includes a base, a trajectory guide frame, and a mounting device. The base is configured to be secured to a body of the patient. The trajectory guide frame includes a targeting cannula. The targeting cannula has an elongate guide bore extending axially therethrough, defining a trajectory axis, and being configured to guide placement of the interventional device. The trajectory guide frame is operable to move the targeting cannula relative to the base to position the trajectory axis to a desired intrabody trajectory to guide placement of the interventional device in vivo. A plurality of patient engagement structures are provided on the base and are configured to penetrate tissue of the body and to space the base apart from the tissue. The system further includes a plurality of fasteners configured to secure the base to the body.

16 Claims, 14 Drawing Sheets

(51) Int. Cl.
*A61B 17/00* (2006.01)
*A61B 17/34* (2006.01)

(56) References Cited

U.S. PATENT DOCUMENTS

| | | | |
|---|---|---|---|
| 4,276,697 A | 7/1981 | Drake et al. |
| 4,319,136 A | 3/1982 | Jinkins |
| 4,386,602 A | 6/1983 | Sheldon et al. |
| 4,838,265 A | 6/1989 | Cosman et al. |
| 5,125,888 A | 6/1992 | Howard et al. |
| 5,154,723 A | 10/1992 | Kubota et al. |
| 5,342,356 A | 8/1994 | Ellman et al. |
| 5,469,847 A | 11/1995 | Zinreich et al. |
| 5,638,819 A | 6/1997 | Manwaring et al. |
| 5,655,084 A | 8/1997 | Pinsky et al. |
| 5,695,501 A | 12/1997 | Carol et al. |
| 5,697,958 A | 12/1997 | Paul et al. |
| 5,699,801 A | 12/1997 | Atalar et al. |
| 5,707,335 A | 1/1998 | Howard et al. |
| 5,728,079 A | 3/1998 | Weber et al. |
| 5,776,144 A | 7/1998 | Leysieffer et al. |
| 5,779,694 A | 7/1998 | Howard et al. |
| 5,855,582 A | 1/1999 | Gildenberg |
| 5,928,145 A | 7/1999 | Ocali et al. |
| 5,961,455 A | 10/1999 | Daum et al. |
| 5,993,463 A | 11/1999 | Truwit |
| 6,006,126 A | 12/1999 | Cosman |
| 6,050,992 A | 4/2000 | Nichols |
| 6,119,032 A | 9/2000 | Martin et al. |
| 6,167,292 A | 12/2000 | Badano et al. |
| 6,167,311 A | 12/2000 | Rezai |
| 6,195,577 B1 | 2/2001 | Truwit et al. |
| 6,206,890 B1 | 3/2001 | Truwit |
| 6,216,030 B1 | 4/2001 | Howard et al. |
| 6,263,229 B1 | 7/2001 | Atalar et al. |
| 6,264,607 B1 | 7/2001 | Goll et al. |
| 6,267,769 B1 | 7/2001 | Truwit |
| 6,267,770 B1 | 7/2001 | Truwit |
| 6,273,896 B1 | 8/2001 | Franck et al. |
| 6,282,437 B1 | 8/2001 | Franck et al. |
| 6,284,971 B1 | 9/2001 | Atalar et al. |
| 6,298,262 B1 | 10/2001 | Franck et al. |
| 6,351,662 B1 | 2/2002 | Franck et al. |
| 6,356,786 B1 | 3/2002 | Rezai et al. |
| 6,368,329 B1 | 4/2002 | Truwit |
| 6,405,079 B1 | 6/2002 | Ansarinia |
| 6,419,680 B1 | 7/2002 | Cosman |
| 6,438,423 B1 | 8/2002 | Rezai et al. |
| 6,526,318 B1 | 2/2003 | Ansarinia |
| 6,529,765 B1 | 3/2003 | Franck et al. |
| 6,539,263 B1 | 3/2003 | Schiff et al. |
| 6,584,351 B1 | 6/2003 | Ekwall |
| 6,591,128 B1 | 7/2003 | Wu et al. |
| 6,606,513 B2 | 8/2003 | Lardo et al. |
| 6,609,030 B1 | 8/2003 | Rezai et al. |
| 6,628,980 B2 | 9/2003 | Atalar et al. |
| 6,675,033 B1 | 1/2004 | Lardo et al. |
| 6,701,176 B1 | 3/2004 | Halperin et al. |
| 6,708,064 B2 | 3/2004 | Rezai |
| 6,725,080 B2 | 4/2004 | Melkent et al. |
| 6,725,092 B2 | 4/2004 | MacDonald et al. |
| 6,752,812 B1 | 6/2004 | Truwit |
| 6,772,000 B2 | 8/2004 | Talpade |
| 6,782,288 B2 | 8/2004 | Truwit et al. |
| 6,904,307 B2 | 6/2005 | Karmarkar et al. |
| 6,920,347 B2 | 7/2005 | Simon et al. |
| 7,022,082 B2 | 4/2006 | Sonek |
| 7,155,316 B2 | 12/2006 | Sutherland et al. |
| 7,167,760 B2 | 1/2007 | Dawant et al. |
| 7,212,611 B2 | 5/2007 | De Godzinsky |
| 7,217,276 B2 | 5/2007 | Henderson et al. |
| 7,235,084 B2 | 6/2007 | Skakoon et al. |
| 7,241,283 B2 | 7/2007 | Putz |
| 7,313,430 B2 | 12/2007 | Urquhart et al. |
| 7,602,190 B2 | 10/2009 | Piferi et al. |
| 7,660,621 B2 | 2/2010 | Skakoon et al. |
| 2001/0004676 A1 | 6/2001 | Ouchi |
| 2001/0014771 A1 | 8/2001 | Truwit et al. |
| 2001/0027271 A1 | 10/2001 | Franck et al. |
| 2001/0047126 A1 | 11/2001 | Nagai et al. |
| 2001/0053879 A1 | 12/2001 | Mills et al. |
| 2002/0010479 A1 | 1/2002 | Skakoon et al. |
| 2002/0019641 A1 | 2/2002 | Truwit |
| 2002/0049451 A1 | 4/2002 | Parmer et al. |
| 2002/0052610 A1 | 5/2002 | Skakoon et al. |
| 2002/0082495 A1 | 6/2002 | Biswal et al. |
| 2003/0028095 A1 | 2/2003 | Tulley et al. |
| 2003/0050557 A1 | 3/2003 | Susil et al. |
| 2003/0055436 A1 | 3/2003 | Daum et al. |
| 2003/0120143 A1 | 6/2003 | Franklin et al. |
| 2003/0205233 A1 | 11/2003 | Aboul-Hosn et al. |
| 2004/0046557 A1 | 3/2004 | Karmarkar et al. |
| 2004/0064148 A1 | 4/2004 | Daum et al. |
| 2004/0092810 A1 | 5/2004 | Daum et al. |
| 2004/0167393 A1 | 8/2004 | Solar et al. |
| 2004/0167543 A1 | 8/2004 | Mazzocchi et al. |
| 2004/0215279 A1 | 10/2004 | Houben et al. |
| 2004/0228796 A1 | 11/2004 | Talpade |
| 2004/0267284 A1 | 12/2004 | Parmer et al. |
| 2005/0004453 A1 | 1/2005 | Tearney et al. |
| 2005/0049486 A1 | 3/2005 | Urquhart et al. |
| 2005/0070781 A1 | 3/2005 | Dawant et al. |
| 2005/0203384 A1 | 9/2005 | Sati et al. |
| 2005/0222647 A1 | 10/2005 | Wahlstrand et al. |
| 2006/0192319 A1 | 8/2006 | Solar |
| 2006/0195119 A1 | 8/2006 | Mazzocchi et al. |
| 2006/0229641 A1 | 10/2006 | Gupta et al. |
| 2006/0252314 A1 | 11/2006 | Atalar et al. |
| 2007/0106305 A1 | 5/2007 | Kao et al. |
| 2007/0118049 A1 | 5/2007 | Viola |
| 2008/0039709 A1 | 2/2008 | Karmarkar |
| 2008/0097193 A1 | 4/2008 | Karmarkar |
| 2008/0306375 A1 | 12/2008 | Sayler et al. |
| 2009/0012388 A1 | 1/2009 | Haerter et al. |
| 2009/0112084 A1* | 4/2009 | Piferi et al. .................. 600/421 |
| 2009/0171184 A1 | 7/2009 | Jenkins et al. |
| 2010/0042111 A1* | 2/2010 | Qureshi et al. ............... 606/130 |
| 2010/0179564 A1* | 7/2010 | Mitchell et al. .............. 606/130 |
| 2014/0024927 A1* | 1/2014 | Piferi ........................... 600/417 |

FOREIGN PATENT DOCUMENTS

| | | |
|---|---|---|
| DE | 100 29 737 A1 | 5/2003 |
| EP | 1 524 626 A | 4/2005 |
| EP | 2 305 109 A1 | 4/2011 |
| WO | WO 98/52064 | 11/1998 |
| WO | WO 01/76498 A2 | 10/2001 |
| WO | WO 03/102614 | 12/2003 |
| WO | WO 2004/029782 | 4/2004 |
| WO | WO 2004/058086 | 6/2004 |
| WO | WO 2006/081409 | 8/2006 |
| WO | WO 2006/099475 A2 | 9/2006 |
| WO | WO 2007/064739 | 6/2007 |
| WO | WO 2007/106558 A2 | 9/2007 |
| WO | WO 2009/146176 A1 | 12/2009 |

OTHER PUBLICATIONS

"Tear Away Introducer Sets (INTRADYN)" B. Braun Medical, Inc., Retrieved Date: May 23, 2007, From URL: http://www.bbraunusa.com/index-5789FECCD0B759A1E3AA1D9D51EC13A5.html?uuid=5789FECCD0B759A1E3AA1D9D51EC13A5, (1 page).

Baker et al., Neurostimulation systems: assessment of magnetic field interactions associated with 1.5- and 3-Tesla MR systems, J Magn Reson Imaging, 2005, 72-77, 21(1).

Bhidayasiri et al., Bilateral neurostimulation systems used for deep brain stimulation: in vitro study of MRI-related heating at 1.5 T and implications for clinical imaging of the brain, Magn Reson Imaging, 2005, 549-555, 23(4).

Buchli et al., Increased RF power absorption in MR imaging due to RF coupling between body coil and surface coil, Magn Reson Med, 1989, 105-112, 9(1).

(56) References Cited

OTHER PUBLICATIONS

Chou et al., RF heating of implanted spinal fusion stimulator during magnetic resonance imaging, IEEE Trans Biomed Eng, 1997, 367-373, 44(5).
Dorward et al., Accuracy of true frameless stereotaxy: in vivo measurement and laboratory phantom studies, J. Neurosurg., 1999, 90:160-168.
Francel, NEXFRAME System, Bilateral Activa® Lead Delivery to STN Using NEXFRAME, Oklahoma University Presbyterian Hospital, Image-Guided Neurologics © 2004, (2 pages).
Grimson et al., An automatic registration method for frameless stereotaxy, image guided surgery, and visualization, IEEE Tran on Medical Imaging, Apr. 1996, 129-140.
Hall et al., Brian biopsy sampling by using prospective stereotaxis and a trajectory guide, J. Neurosurg., 2001, 94:67-71.
International Search Report (5 pages) corresponding to PCT/US2006/045752; Mailing Date: Sep. 28, 2007.
International Search Report and Written Opinion (14 pages) corresponding to International Application No. PCT/US2008/011051; Mailing Date: Feb. 11, 2009.
Invitation to Pay Additional Fees and, Where Applicable, Protest Fee (8 pages) corresponding to International Application No. PCT/US2008/011050; Mailing Date: Mar. 10, 2009.
Invitation to Pay Additional Fees and, Where Applicable, Protest Fee (6 pages) corresponding to International Application No. PCT/US2008/011040; Mailing Date: Dec. 19, 2008.
Invitation to Pay Additional Fees and, Where Applicable, Protest Fee for PCT Application No. PCT/US2008/007169, mailed Nov. 19, 2008.
Jorgensen, Erik, Brain Image Analsis Team Joins SCI Institute, http://www.sci.utah.edu/stories/2007/Gerig_NeuroimageAnalysis.html, (2007), 3 Pages.
Ladd et al., Reduction of resonant RF heating in intravascular catheters using coaxial chokes, Magn Reson Med, 2000, 615-619, 43(4).
Lin et al., "A Wavelet-Based Approximation of Surface Coil Sensitivity Profiles for Correction of Image Intensity Inhomogeneity and Parallel Imaging Reconstruction," *Human Brain Mapping* 2003, 19(2):96-111.
Liu et al., Remotely-Controlled Approach for Stereotactic Neurobiopsy, Computer Aided Surgery, 2002, 7:237-247.
Luechinger et al., In vivo heating of pacemaker leads during magnetic resonance imaging, Eur Heart J, 2005, 376-383, 26(4).
Martin et al., Placement of Deep Brain Stimulator Electrodes Using Real-Time High-Field Interventional Magnetic Resonance Imaging, Magnetic Resonance in Medicine, 2005, 54:1107-1114.
Martin, Can cardiac pacemakers and magnetic resonance imaging systems co-exist?, Eur Heart J, 2005, 325-327, 26(4).
Notification of Transmittal of the International Search Report and the Written Opinion of the International Searching Authority, or the Declaration (23 pages) corresponding to PCT/US2008/011050; Mailing Date: Jun. 24, 2009.
Notification of Transmittal of the International Search Report and the Written Opinion of the International Searching Authority, or the Declaration (22 pages) corresponding to PCT/US2008/011040; Mailing Date: Apr. 27, 2009.
Notification of Transmittal of the International Search Report and the Written Opinion of the International Searching Authority, or the Declaration (18 pages) corresponding to PCT/US2008/007169; Mailing Date: Mar. 12, 2009.
Rezai et al., Neurostimulators: potential for excessive heating of deep brain stimulation electrodes during magnetic resonance imaging, J Magn Reson Imaging, 2001, 488-489, 14(4).
Sauser, Brittany, A 3-D View of the Brain, http://www.technologyreview.com/Biotech/19140, Aug. 6, 2007, 3 Pages.
Singh et al., "Accurate Intensity Correction for Endorectal Surface Coil MR Imaging of the Prostate," IEEE Transactions on Nuclear Science, 1993, 40(4):1169-1173.
Smith et al., The Neurostation—A Highly Accurate, Minimally Invasive Solution to Frameless Stereotactic Neurosurgery, Computerized Medical Imaging and Graphics, 1994, 247-256, 18(4).
STarFix™—Dr. Joel Franck and FHC engineer Ron Franklin—creators, www.tgt.vanderbilt.edu/reu2/REU2002/chris.ppt (19 pages).
Truwit et al., Prospective Stereotaxy: A Novel Method of Trajectory Alignment Using Real-Time Image Guidance, J. Magn. Reson. Imag., 2001, 13:452-457.
Willems et al., Frameless Stereotaxy, VHL Family Alliance, From URL: http://www.vhl.org/newsletter/vhl2000/00aefrst.htm, *VHL Family Forum* 8:1, Mar. 2000, (3 pages).
Wirtz et al., Image-Guided Neurosurgery with Intraoperative MRI: Update of Frameless Stereotaxy and Radicality Control, Sterotact Funct Neurosurg 1997, 68:39-43.
Yoda, Decoupling technique for transmit coils in NMR spectroscopy and imaging, NMR Biomed, 1990, 27-30, 3(1).
Notification Concerning Transmittal of International Preliminary Report on Patentability in corresponding PCT Application No. PCT/US2013/057932; Date of Mailing: Mar. 10, 2015; 7 pages.

* cited by examiner

TRAJECTORY GUIDE FRAME FOR MRI-GUIDED SURGERIES

RELATED APPLICATION(S)

The present application claims the benefit of and priority from U.S. Provisional Patent Application No. 61/697,090, filed Sep. 5, 2012, the disclosure of which is incorporated herein by reference in its entirety.

FIELD OF THE INVENTION

The present invention relates generally to medical devices and methods and, more particularly, to MRI-guided devices and methods.

BACKGROUND OF THE INVENTION

It is often necessary or desirable to mount a trajectory guide frame for MRI-guided surgeries directly to a patient. For example, a frameless stereotactic trajectory guide apparatus may be secured to a patient's skull using bone penetrating screws or the like. Examples of such trajectory guide apparatus are disclosed in U.S. Published Patent Application No. 2009/0112084 A1.

SUMMARY OF THE INVENTION

According to embodiments of the present invention, an MRI-guided interventional system for use with a patient and an interventional device includes a base, a trajectory guide frame, and a mounting device. The base is configured to be secured to a body of the patient. The trajectory guide frame includes a targeting cannula. The targeting cannula has an elongate guide bore extending axially therethrough, defining a trajectory axis, and being configured to guide placement of the interventional device. The trajectory guide frame is operable to move the targeting cannula relative to the base to position the trajectory axis to a desired intrabody trajectory to guide placement of the interventional device in vivo. A plurality of patient engagement structures are provided on the base and are configured to penetrate tissue of the body and to space the base apart from the tissue. The system further includes a plurality of fasteners configured to secure the base to the body.

According to some embodiments, the fasteners are screws.

According to some embodiments, the MRI-guided interventional system is configured for use with a head of the patient, the head having a skull covered by a scalp, the base is configured to be secured to the head such that the plurality of patient engagement structures penetrate the scalp and space the base apart from the skull, and the plurality of screws are configured to secure the base to the skull.

According to method embodiments of the present invention, a method for mounting an MRI-guided interventional system on a patient includes providing an MRI-guided interventional system including: a base configured to be secured to a body of the patient; a trajectory guide frame including a targeting cannula, the targeting cannula having an elongate guide bore extending axially therethrough, defining a trajectory axis, and being configured to guide placement of the interventional device, wherein the trajectory guide frame is operable to move the targeting cannula relative to the base to position the trajectory axis to a desired intrabody trajectory to guide placement of the interventional device in vivo; a plurality of patient engagement structures on the base; and a plurality of fasteners configured to secure the base to the body. The method further includes: mounting the base on the body such that the patient engagement structures penetrate tissue of the body and space the base apart from the tissue; and securing the base to the body using the plurality of fasteners.

According to some embodiments, the fasteners are screws.

According to some embodiments, the MRI-guided interventional system is configured for use with a head of the patient, the head having a skull covered by a scalp, mounting the base on the head includes mounting the base on the head such that the plurality of patient engagement structures penetrate the scalp and space the base apart from the skull, and securing the base to the body using the plurality of screws includes securing the base to the skull using the plurality of screws. In some embodiments, the screws penetrate the scalp.

In some embodiments, the step of securing the base to the skull using a plurality of screws includes driving the screws through the scalp and into the skull.

Further features, advantages and details of the present invention will be appreciated by those of ordinary skill in the art from a reading of the figures and the detailed description of the embodiments that follow, such description being merely illustrative of the present invention.

DESCRIPTION OF EMBODIMENTS OF THE INVENTION

Figure 1:
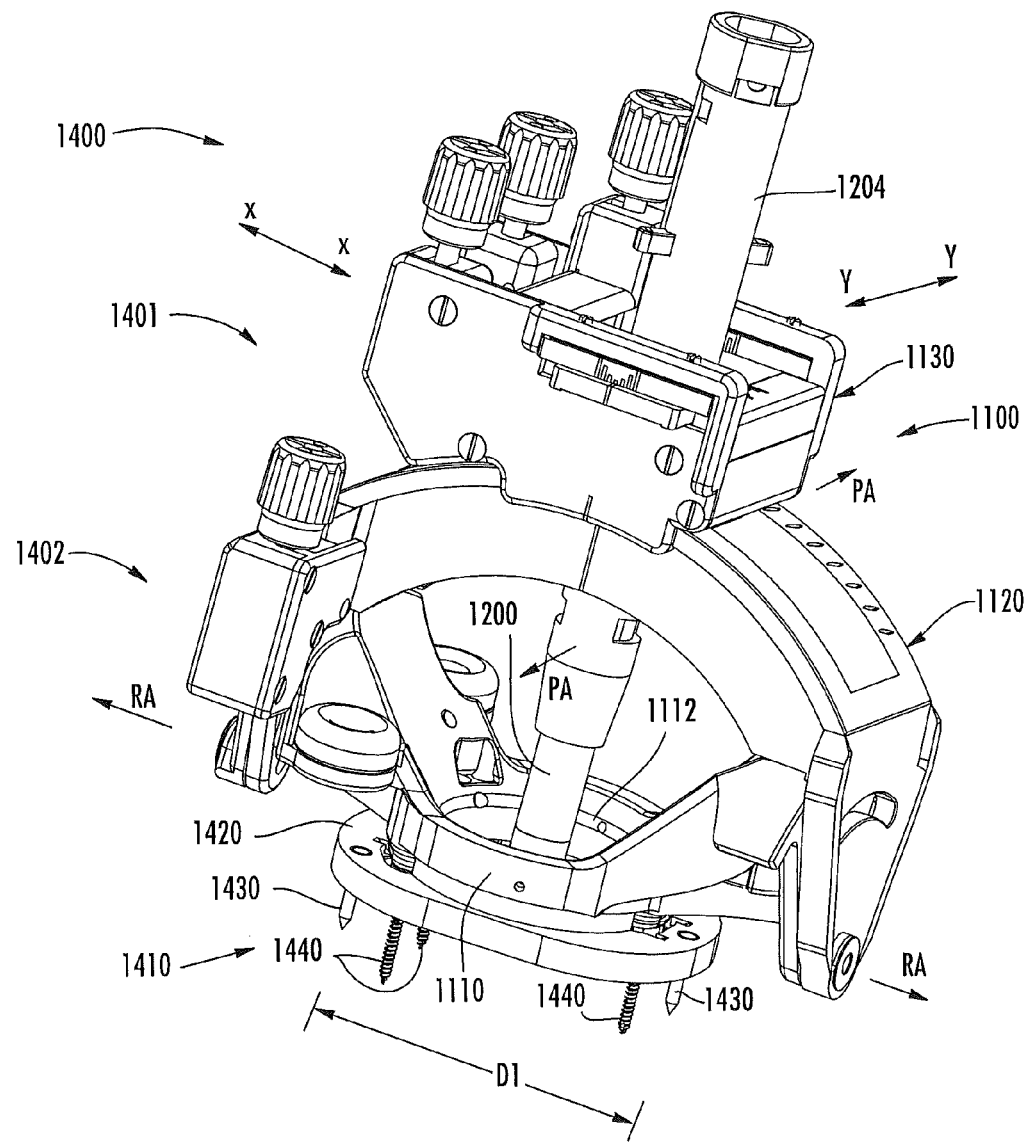
FIG. 1 is a perspective view of a trajectory guide frame assembly according to embodiments of the present invention.

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

The term "fiducial marker" refers to a marker that can be electronically identified using image recognition and/or electronic interrogation of MRI image data. The fiducial marker can be provided in any suitable manner, such as, but not limited to, a geometric shape of a portion of the tool, a component on or in the tool, a coating or fluid-filled component or feature (or combinations of different types of fiducial markers) that makes the fiducial marker(s) MRI-visible with sufficient signal intensity (brightness) or generates a "void" or dark space for identifying location and/or orientation information for the tool and/or components thereof in space.

The term "MRI scanner" refers to a magnetic resonance imaging and/or NMR spectroscopy system. As is well known, MRI scanners include a low field strength magnet (typically between about 0.1 T to about 0.5 T), a medium field strength magnet, or a high-field strength super-conducting magnet, an RF pulse excitation system, and a gradient field system. MRI scanners are well known to those of skill in the art. Examples of commercially available clinical MRI scanners include, for example, those provided by General Electric Medical Systems, Siemens, Philips, Varian, Bruker, Marconi, Hitachi and Toshiba. The MRI systems can be any suitable magnetic field strength, such as, for example, about 1.5 T or about 3.0 T, and may include other high-magnetic field systems between about 2.0 T-10.0 T.

The term "MRI visible" means that the device is visible, directly or indirectly, in an MRI image. The visibility may be indicated by the increased SNR of the MRI signal proximate the device.

The term "MRI compatible" means that the so-called component(s) is suitable for use in an MRI environment and as such is typically made of a non-ferromagnetic MRI compatible material(s) suitable to reside and/or operate in or proximate a conventional medical high magnetic field environment. The "MRI compatible" component or device is "MR safe" when used in the MRI environment and has been demonstrated to neither significantly affect the quality of the diagnostic information nor have its operations affected by the MR system at the intended use position in an MR system. These components or devices may meet the standards defined by ASTM F2503-05. See, American Society for Testing and Materials (ASTM) International, Designation: F2503-05. Standard Practice for Marking Medical Devices and Other Items for Safety in the Magnetic Resonance Environment. ASTM International, West Conshohocken, Pa., 2005.

Embodiments of the present invention are directed to trajectory guide frames and assemblies (and systems and methods including the same) for MRI-guided medical interventions such as disclosed in U.S. Published Patent Application No. 2009/0112084 A1 (hereinafter referred to as "the '084 publication"). The disclosures of the '084 publication and the counterpart PCT application published as WO2009/042130 A2 are hereby incorporated herein by reference in their entireties.

With reference to FIG. 1, a trajectory guide frame system 1400 according to embodiments of the present invention is shown therein. The system 1400 includes a trajectory guide frame 1100 (e.g., as described in the '084 publication) and a mounting device 1410 (which can take the form of an adapter, base support, base extension, stabilizer structure, submount, or support assembly as illustrated, for example). Generally and as discussed in more detail herein, the mounting device 1410 can be coupled to the trajectory guide frame 1100 to form a trajectory guide frame assembly 1401 and serves to facilitate securement of the trajectory guide frame 1100 to a patient. According to some embodiments, the mounting device 1410 is used to facilitate securement of trajectory guide frame 1100 to a skull M (FIG. 5) of the patient. Once mounted, the assembly 1401 can be used in the same manner and for the same purposes as disclosed for the trajectory guide frame 1100 in the '084 publication, for example.

Figure 6:
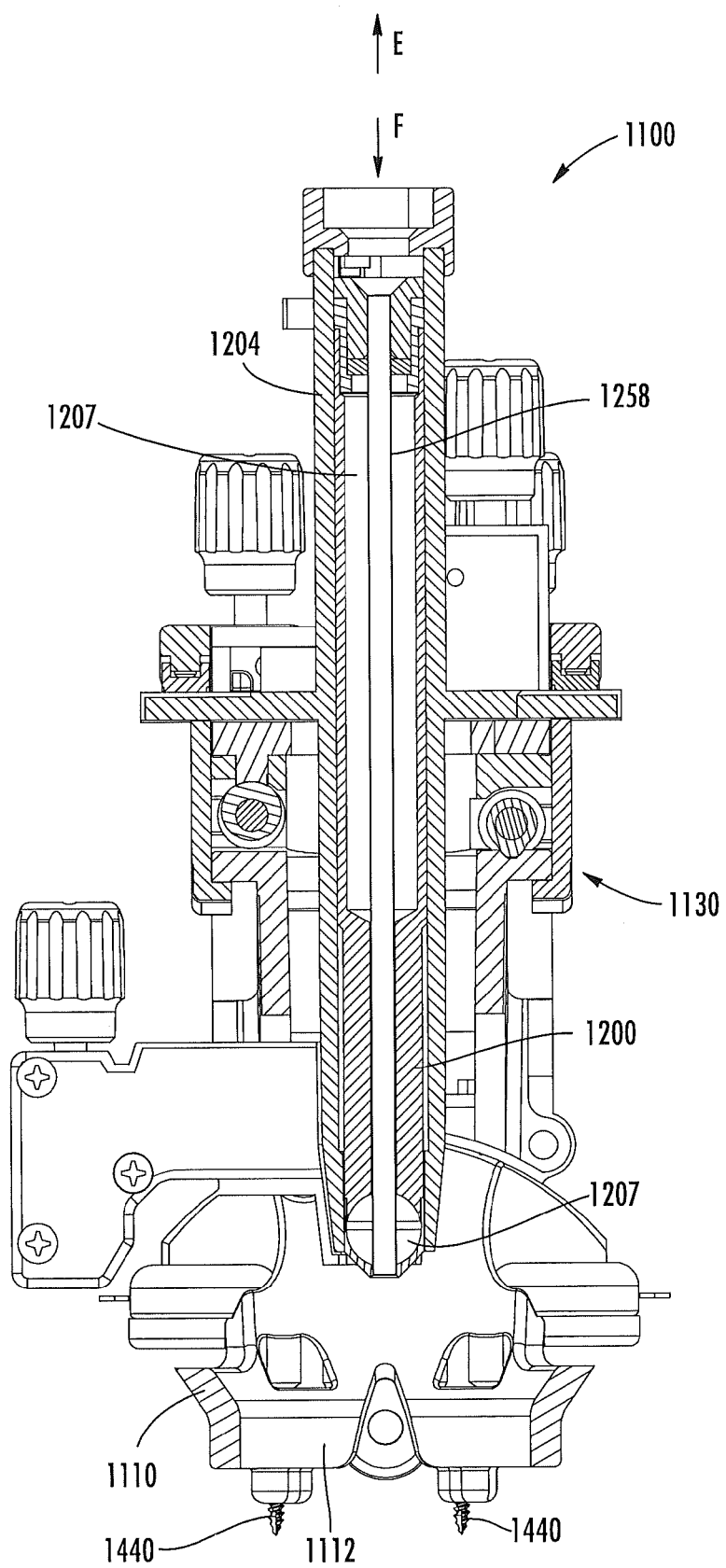
FIG. 6 is a cross-sectional view of a portion of the trajectory guide frame assembly of FIG. 1.

As discussed in the '084 publication and with reference to FIGS. 1 and 6-9, the trajectory guide frame 1100 includes a base portion 1110, a yoke 1120, a platform 1130, a targeting cannula 1200 (FIGS. 1 and 6), and a tubular trajectory guide member 1204. The targeting cannula 1200 has a guide lumen tube 1258 (FIG. 6) to receive an interventional device. The targeting cannula 1200 can slide up and down (in directions E and F; FIG. 6) in the passage of the targeting cannula guide member 1204. The platform 1130 may be movably mounted on the yoke 1120 to rotate about on pitch axis PA-PA (FIG. 1). The yoke 1120 may in turn be movably mounted on the base portion 1110 to rotate or pivot about a roll axis RA-RA transverse (in some embodiments, perpendicular) to the pitch axis PA-PA. The platform 1130 may be further configured to selectively translate the trajectory guide member 1204 (and thereby the targeting cannula 1200) along each of an X-axis and a Y-axis (FIG. 1) relative to the yoke 1120. Various local or remote control mechanisms or actuators (e.g., as disclosed in the '084 publication) can be provided to provide the foregoing adjustments.

The frame 1100 includes a mounting system 1101 (FIG. 7) configured to allow assembly of the yoke 1120 onto the base portion 1110 by an operator or the like when desired. According to some embodiments, the mounting system 1101 also permits the yoke 1120 to be dismounted from the base portion 1110 when desired.

Figure 7:
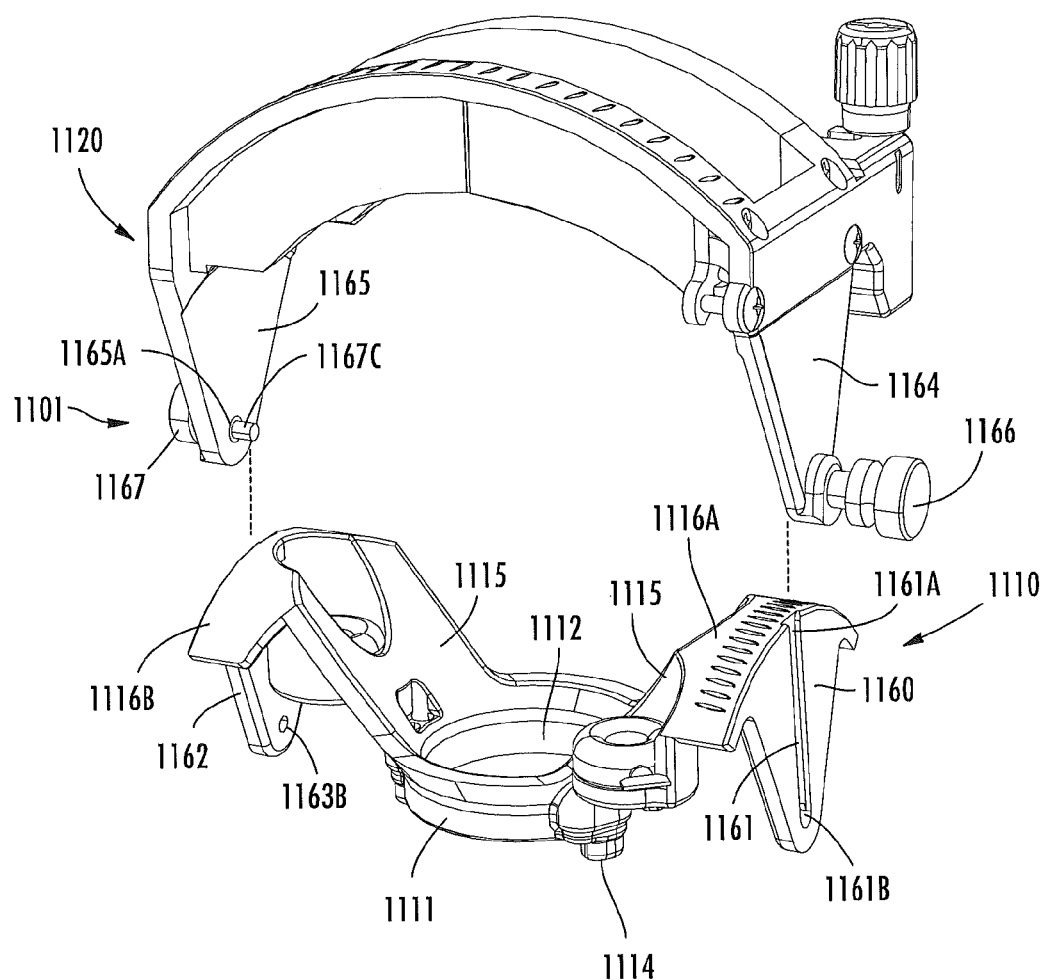
FIGS. 7 and 8 are opposed, top perspective views of a yoke and a base portion forming parts of the trajectory guide frame assembly of FIG. 1.
Figure 8:
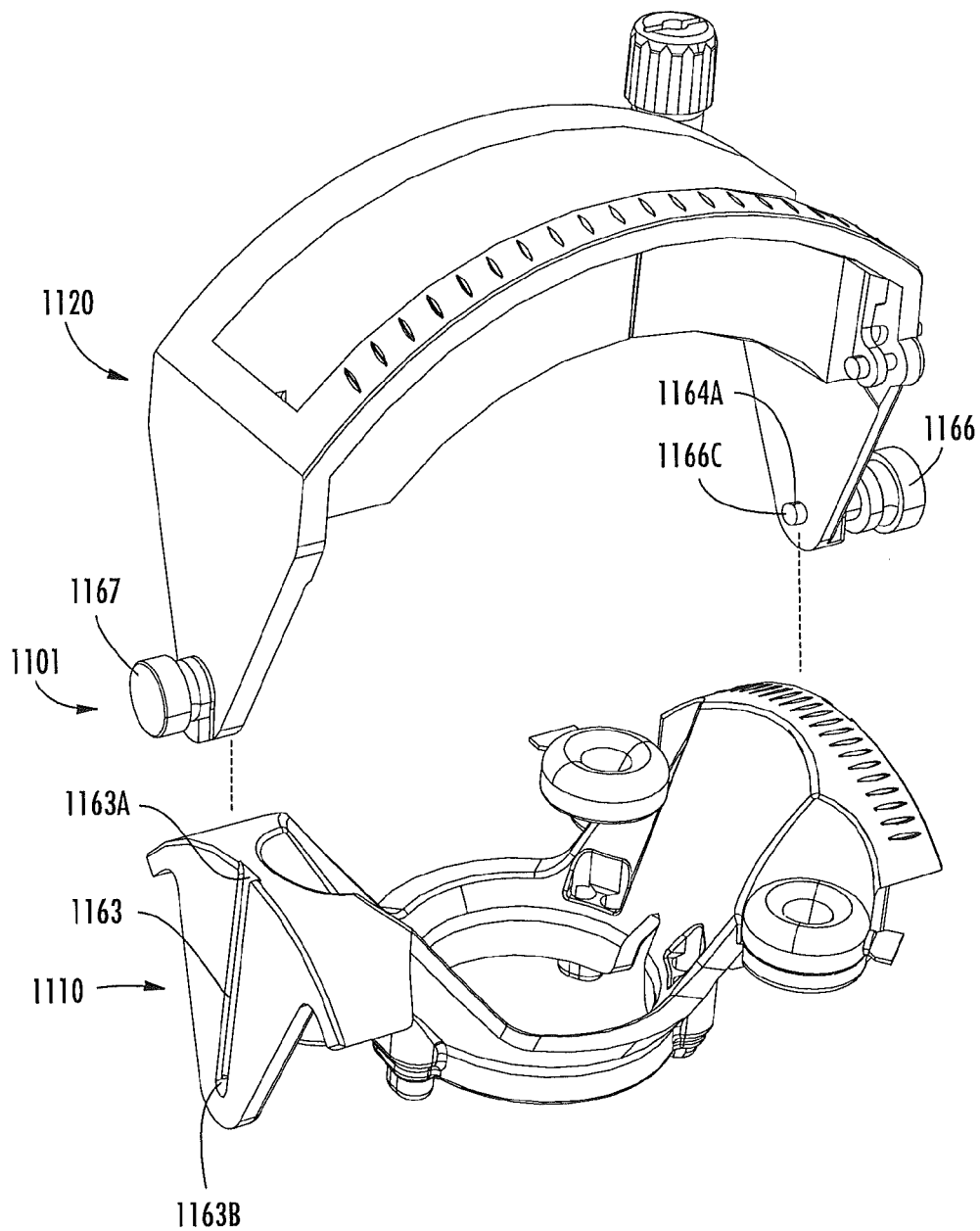
Figure 9:
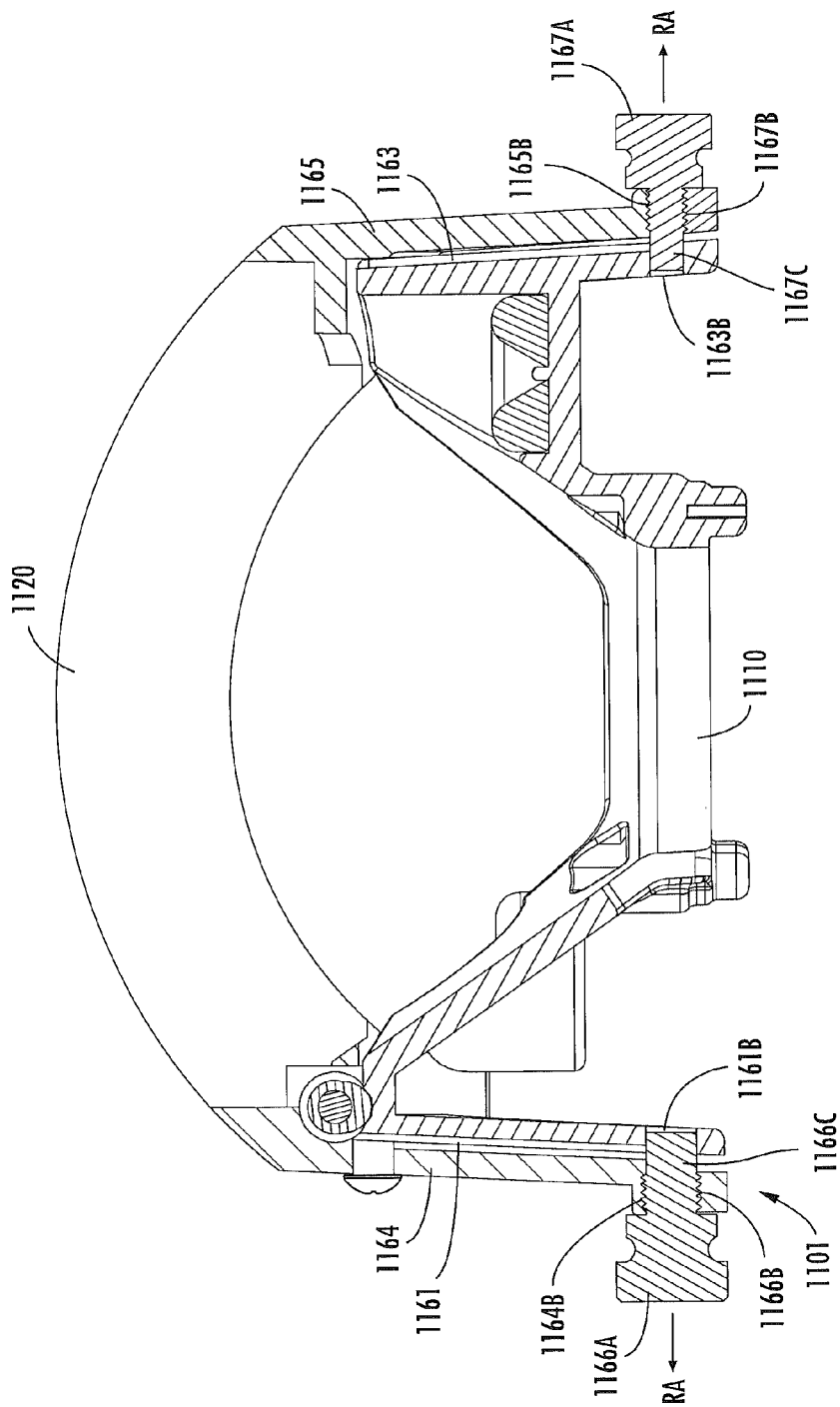
FIG. 9 is a cross-sectional view of the yoke and base portion of FIGS. 7 and 8.

With reference to FIGS. 7-9, a first part of the mounting system 1101 is integrated into the base portion 1110. The base portion 1110 includes a hub 1111 defining the patient access opening 1112 and which can be secured to the patient by fasteners 1440 (FIG. 1) inserted through the screw holes 1114. According to some embodiments and as shown, the fasteners 1440 are screws. An interventional device can be inserted through the lumen 1258 and further through the access opening 1112. Two struts 1115 extend from the hub 1111 to support first and second arcuate rails or arms 1116A and 1116B. A first mount tab or extension 1160 depends from the first arm 1116A and a second mount tab or extension 1162 depends from the second arm 1116B. A generally vertical first mount slot 1161 is provided in the first extension 1160 (accessible via the outer wall). The first mount slot 1161 has a slot inlet 1161A on its upper end and a pivot hole 1161B on its lower end. A generally vertical second mount slot 1163 is provided in the second extension 1162. The second mount slot 1163 has a slot inlet 1163A on its upper end and a pivot hole 1163B on its lower end.

The yoke 1120 has first and second depending mount wings, tabs or arms 1164 and 1165. As shown in FIGS. 7-9, a mount hole 1164A (FIG. 8) is formed in the mount arm 1164 and has internal threads 1164B. A mount hole 1165A (FIG. 7) is formed in the mount arm 1165 and has internal threads 1165B.

As shown in FIGS. 7-9, the mounting system 1101 further includes first and second pivot screws 1166 and 1167 each including a respective knob 1166A, 1167A, an externally threaded shank 1166B, 1167B, and a smooth pivot pin or post 1166C, 1167C. The first pivot screw 1166 is screwed into the first mount hole 1164A such that the pivot post 1166C projects inwardly beyond the hole 1164A. The second pivot screw 1167 is screwed into the second mount hole 1165A such that the pivot post 1167C projects inwardly beyond the hole 1165A.

According to some embodiments, the yoke 1120 is mounted on the base portion 1110 before the base portion 1110 is mounted on the patient and, according to some embodiments, after the frame 1100 components are shipped from the manufacturer to the end user.

To assemble the frame 1100, the yoke 1120 can be mounted on the base portion 1110 as follows. With the pivot screws 1166, 1167 installed in the holes 1164A, 1165A and the opposed posts 1166C, 1167C projecting inwardly toward one another, the posts 1166C and 1167C are positioned above the slots 1161, 1163 and aligned with the slot inlets 1161A and 1163A, respectively. The yoke 1120 is lowered onto the arcuate arms 1116 of the base portion 1110 such that the posts 1166C and 1167C slide into the slots 1161 and 1163, respectively, through the slot inlets 1161A and 1163A. The assembler continues to lower the yoke 1120 so that the posts 1166C, 1167C slide down the slots 1161, 1163 until the posts 1166C and 1167C align with the pivot holes 1161B and 1163B, respectively, whereupon the posts 1166C and 1167C seat within the pivot holes 1161B and 1163B. The yoke 1120 is thereby mounted on the base portion 1110 to pivot about the roll axis RA (i.e., about the pivot posts 1166C, 1167C) relative to the base portion 1110. If desired, the yoke 1120 can be dismounted from the base portion 1110 by pulling the mount arms 1164, 1165 apart to release the posts 1166C, 1167C from the pivot holes 1161B, 1163B and sliding the posts 1166C, 1167C back up and out of the slots 1161, 1163. The pivot screws 1166, 1167 can be screwed outwardly so that it is not necessary to spread the arms 1164, 1165 to release the posts 1166C, 1167C. If desired, the screws 1166, 1167 can be fully removed from the yoke 1120. The knobs 1166A, 1167A can be grasped and pulled by the operator to pull the arms 1164, 1165 apart.

MRI-visible fiducial materials or markers 1109 (FIG. 2) may be mounted on the base portion 1110 and MRI-visible material or markers 1207 (FIG. 6) may be mounted on the targeting cannula 1200 (e.g., in the form of cavities filled with MRI-visible liquid). The fiducial markers 1109, 1207 may be used to track, monitor, and control the position of the targeting cannula 1200 using MRI guidance as described in the '084 publication, for example.

The mounting device 1410 includes a mounting member 1420 and three stabilizer or patient engagement structures 1430 (hereinafter "pins 1430"), which may take the form of mounting posts, spacers, or pins.

Figure 2:
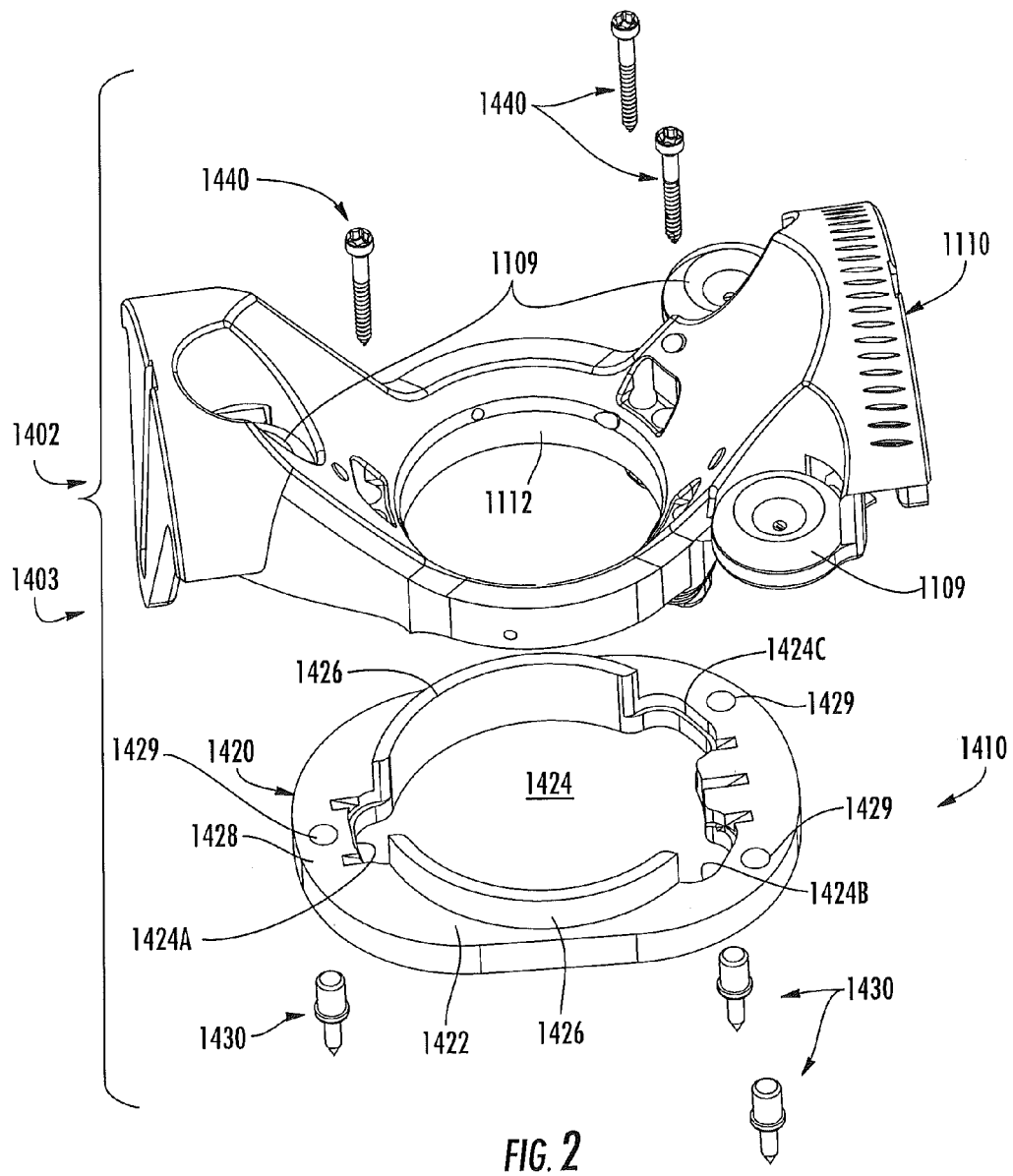
FIG. 2 is an exploded, top perspective view of a subassembly forming a part of the trajectory guide frame of FIG. 1.
Figure 3:
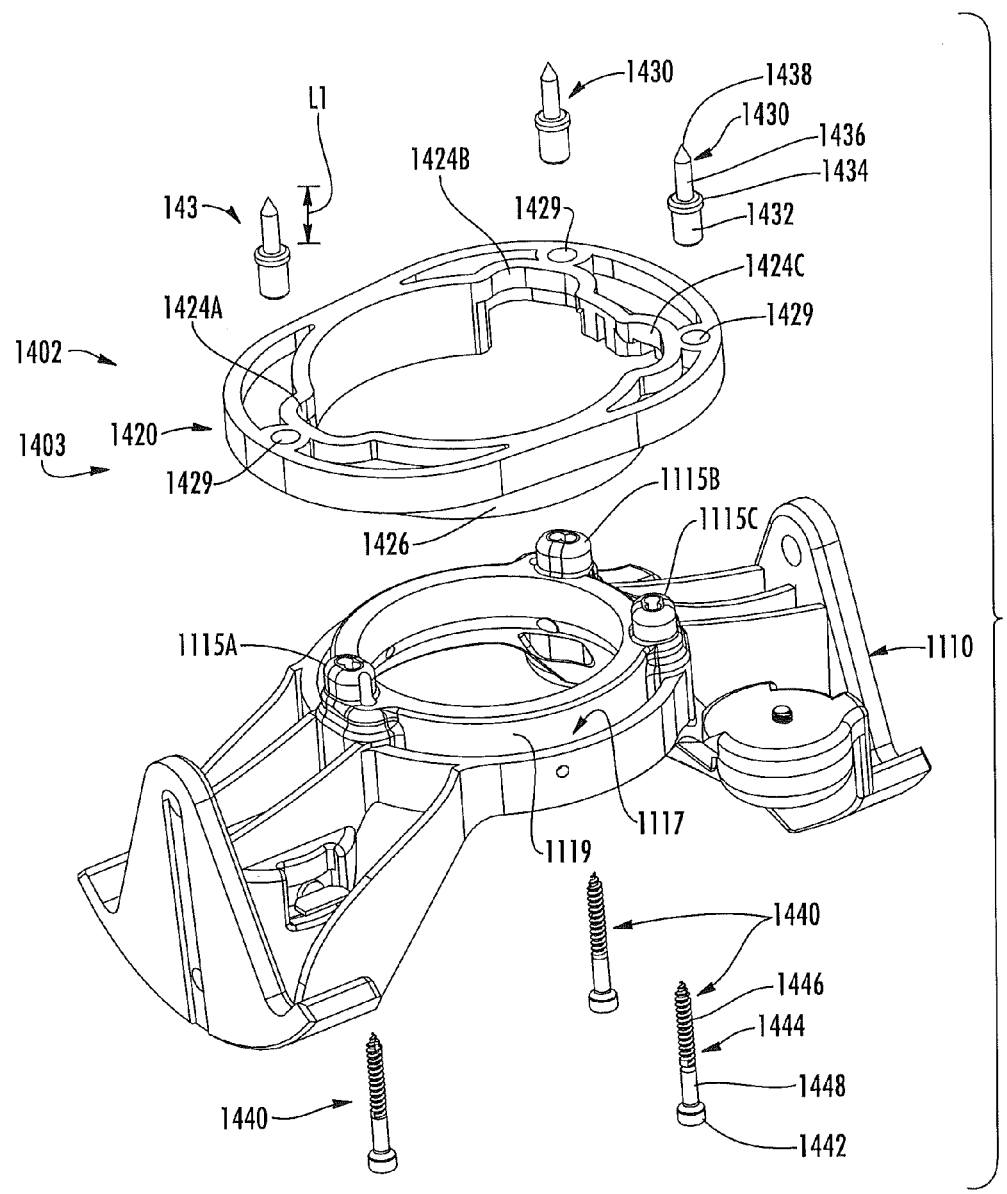
FIG. 3 is an exploded, bottom perspective view of the subassembly of FIG. 2.
Figure 4:
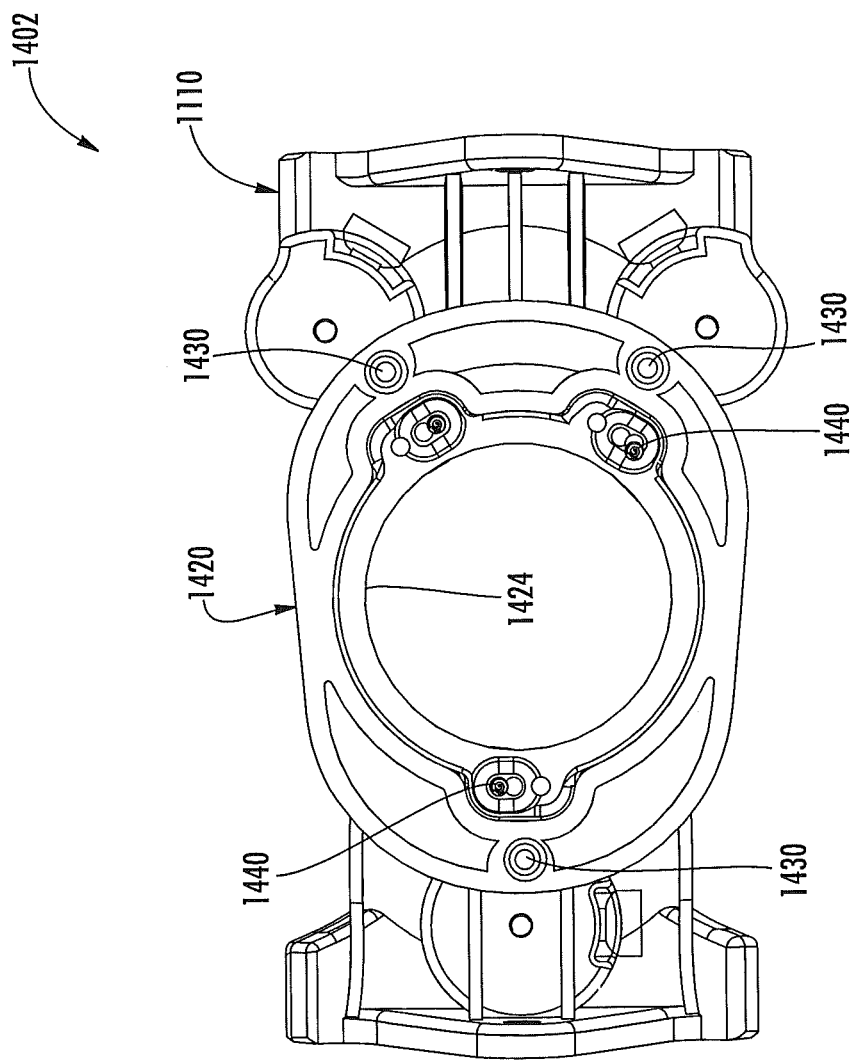
FIG. 4 is a bottom plan view of the subassembly of FIG. 2.

With reference to FIGS. 2-4, the mounting member 1420 includes an annular body 1422 defining a receiver or access opening 1424 and three locator recesses 1424A-C contiguous with and spaced apart about a perimeter of the opening 1424. A coupling flange 1426 extends upwardly from the body 1422 and an extension flange 1428 extends laterally or radially outwardly from the body 1422. Pin mount bores 1429 are provided in the extension flange 1428 to each receive and hold a respective one of the pins 1430. The mounting member 1420 may be formed of any suitable MRI-compatible and/or MRI safe material, such as any non-ferromagnetic material and is typically a substantially rigid polymeric material. The mounting member 1420 may be formed of molded polycarbonate, for example.

Each pin 1430 (FIG. 3) includes a mount post 1432 (seated in a respective bore 1429), a locator flange 1434, and a spacer or engagement section 1436 having a tip 1438. In some embodiments and as illustrated, each engagement section 1436 conically tapers down to a relatively sharp tip 1438. According to some embodiments, the tips 1438 are capable of piercing and penetrating through a scalp upon application of a pressing load by hand. The pins 1430 may be formed of any suitable MRI-compatible and/or MRI safe material, such as machined titanium, for example.

Referring again to the base portion 1110 (FIG. 3), a downwardly projecting screw post 1115A-C is associated with and surrounds each screw hole 1114. A downwardly projecting annular flange 1119 defines an annular coupling slot 1117 in the lower side of the base portion 1110.

Each screw 1440 (FIG. 3) includes a head 1442 (configured to operatively engage a driver) and a shank 1444. As discussed below, when installed, each screw 1440 will have a portion 1446 of its shank 1444 that is embedded in the patient's skull M (or other tissue, when the mounting device 1410 is used for a procedure targeting another part of the patient) and a portion 1448 that protrudes above the patient's skull M (or other targeting entry location). According to some embodiments, at least the portion 1446 is threaded and, in some embodiments, the portion 1448 is not threaded and has an outer diameter at least as great as the outer diameter of the thread of the portion 1446. According to some embodiments, the lead end of the screw thread 1446 is self-tapping. The screws 1440 may be formed of any suitable MRI-compatible and/or MRI safe material, such as machined titanium, for example.

Figure 5:
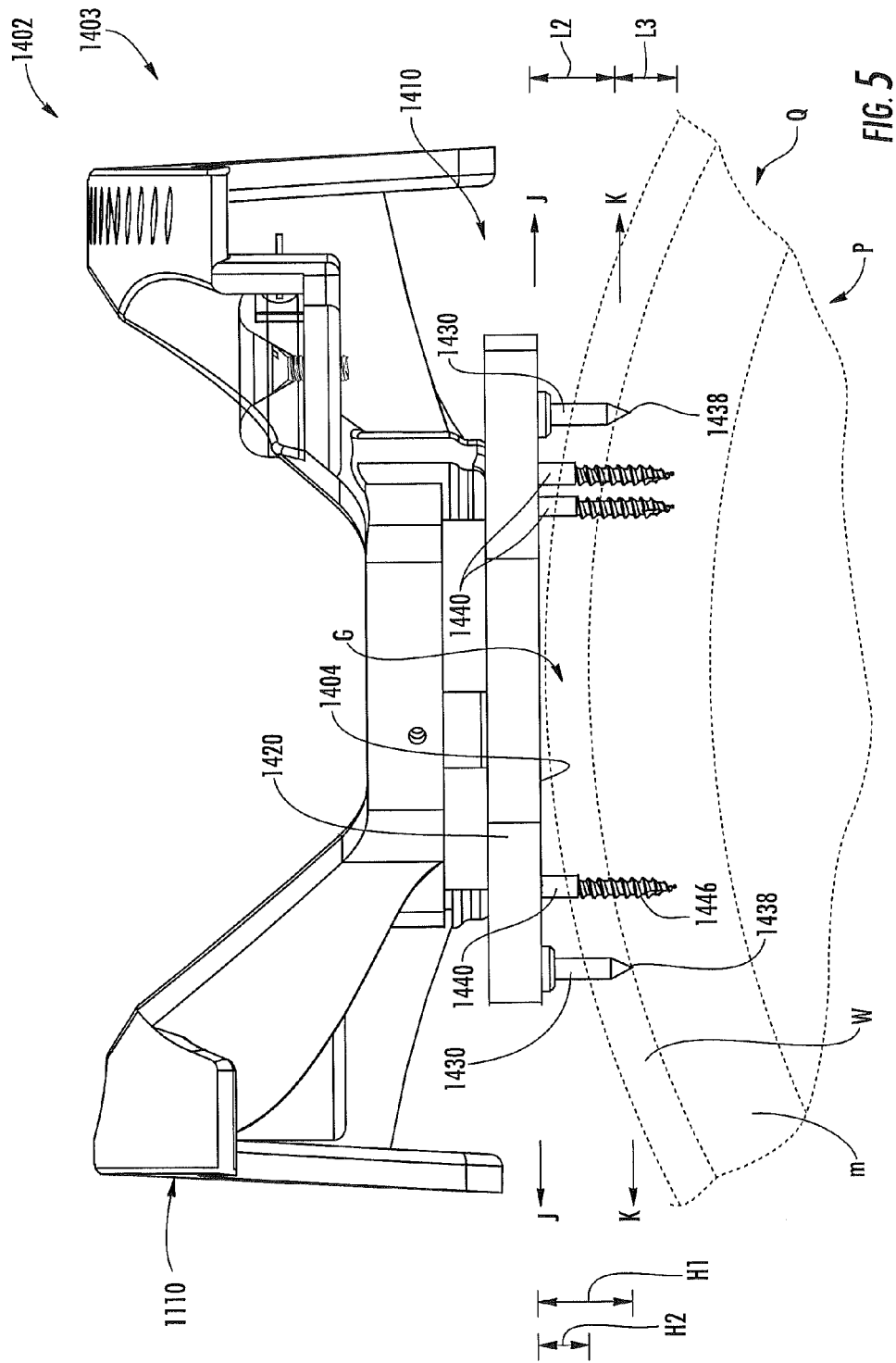
FIG. 5 is a front view of the subassembly of FIG. 2 mounted on a patient.

The system 1400 may be used as follows in accordance with methods of the present invention to form the assembly 1401 and thereby operatively secure the trajectory guide frame 1100 to the skull M of the patient P (FIG. 5). Although described for use with a head (e.g., for brain surgeries), according to other embodiments, the system 1400 may be used to operatively secure the trajectory guide frame 1100 to a selected location on the patient P other than the skull M.

The pins 1430 are secured in the bores 1429 (this may be accomplished at the factory or in the field). The mounting member 1420 is mounted on the base portion 1110 to form a subassembly 1402 including a base 1403 (formed by the base portion 1110 and the mounting member 1420). More particularly, the mounting member 1420 and the base portion 1110 are mated such that the base flange 1119 is snugly received in the mounting device opening 1424, the mounting device coupling flange 1426 is received in the base coupling slot 1117, and the screw posts 1115A-C are each received in a respective one of the recesses 1424A-C. In some embodiments, snap fit or interlock features are provided to secure the components 1420, 1110 together in this configuration. In some embodiments, an interference fit serves to secure the components 1420, 1110 together in this configuration; and, in some embodiments, the components 1420, 1110 are not secured together until the assembly 1401 is secured to the skull M by the screws 1440.

As shown in FIG. 5, the subassembly 1402 is placed on the scalp N of the patient's head Q such that the access opening 1112 (FIG. 4) is positioned over the location to be opened. In some embodiments, the subassembly 1402 is pre-pressed onto the scalp N to drive the pin tips 1438 down into the scalp N all the way to (and in abutment with) the skull M or to a position proximate the skull M. According to some alternative embodiments, the mounting device 1410 is placed on the scalp N (and may be pre-pressed into the scalp N) prior to mating the base portion 1110 to the mounting member 1420.

The screws 1440 may be pre-installed in the screw holes 1114 (e.g., as packaged) or subsequently inserted. With the subassembly 1402 in place and the screws 1440 inserted through the screw holes 1114, the screws 1440 are driven through the scalp N and into the skull M as shown in FIG. 5. The assembly 1401 is thereby formed and secured to the skull M.

The yoke 1120 platform 1130, targeting cannula 1200, and targeting cannula guide member 1204 can be mounted on the base portion 1110 (before or after mounting the assembly 1401 on the skull M) and the trajectory guide frame 1100 may be used in the manner disclosed in the '084 publication, for example. More particularly, the targeting cannula 1200 can be selectively positioned and repositioned by sliding it in the upward direction E and the downward direction F in the guide member 1204, pivoting the yoke 1120 about the roll axis RA-RA, rotating the platform 1130 about the pitch axis PA-PA, translating the guide member 1204 along the X-axis on the platform 1130, and/or translating the guide member 1204 along the Y-axis on the platform 1130. Once the targeting cannula 1200 is positioned as desired, an interventional device can be inserted through the lumen 1258 along the selected trajectory and into the patient P. According to some embodiments, the positioning of the targeting cannula 1200 is conducted in an MRI scanner and is MRI-guided.

In some embodiments, the procedure is continued using a burr hole formed in the skull M as an access portal to the brain and employing the trajectory guide frame 1100 affixed to the skull of the patient. The trajectory guide frame 1100 may allow the operator to align an access path trajectory to a predetermined internal target site, such that the interventional/surgical device/lead, therapy, etc. will be delivered to the target site following the desired trajectory (e.g., a planned trajectory line) through the cranial tissue. This trajectory goes through an entry location point. The interventional device (e.g., probe, lead or the like) can be advanced through the targeting cannula 1200 of the trajectory guide frame 1100, into the head and to or proximate the target point. In some embodiments, the trajectory guide frame 1100 can pivot the targeting cannula 1200 about a pivot point at or proximate the entry point location. The trajectory guide frame 1100 may be remotely repositioned using a trajectory guide apparatus controller, for example.

An incision may be formed in the scalp N through the access opening 1112 before or after the assembly 1401 has been installed on the skull M. A burr hole may be formed (e.g., by drilling) in the skull M before or after mounting the assembly 1401 on the skull M.

In some embodiments, the assembly 1401 and the trajectory guide frame 1100 are mounted on the skull M as described, the targeting cannula 1200 is aligned (if needed with the skull M as desired, and the trajectory guide frame 1100 is used as a drill guide for a drill bit that is inserted through the access opening 1112 to form the burr hole. The guide member 1204, the targeting cannula 1200, or a supplemental drill guide (inserted in the guide member 1204 in place of the targeting cannula 1200) may be used to receive and guide the drill bit. Exemplary methods and apparatus for using a trajectory guide frame as described herein to guide a drill bit for forming a burr hole are disclosed in U.S. patent application Ser. No. 13/781,049, filed Feb. 28, 2013, the disclosure of which is incorporated herein.

With reference to FIG. 5, the lower surface 1404 of the mounting member 1420 or the base portion 1110 (whichever is lowest) defines a frame plane J-J and the tips 1438 of the pins 1430 define a skull engagement plane K-K. As can be seen in FIG. 6, the pins 1430 space the plane J-J a prescribed distance or height H1 from the plane K-K, and thereby from the points on the skull M contacted by the pins 1430. In this way, the pins 1430 can space or standoff the lower surface 1404 (and, hence, the base portion 1110) from the skull M to create a gap G therebetween. The height 112 of the gap G may vary depending on the curvature or profile of the skull M in the mounting region.

According to some embodiments, the height H1 is selected to ensure that in any intended application, the height 112 will be sufficient to prevent the lower surface 1404 from unduly clamping or pinching the scalp N.

According to some embodiments, the height H1 is in the range of from about 5 mm to 20 mm.

By spacing the base 1403 (i.e., the base portion 1110 and the mounting member 1420) off of the scalp N, the base 1403 is provided with a stable attachment and is prevented from placing pressure on the scalp N. Such pressure is undesirable as it may make the base and the trajectory guide frame 1100 unstable, and may compress the scalp N or other tissue, causing it to die. Moreover, it is not necessary to peel back a large area of the scalp N to expose the skull M to directly mate the base portion 1110 to the skull M.

The mounting device 1410 can also serve to stabilize the trajectory guide frame 1100 during and after mounting on the skull M. During installation, the mounting device 1410 sets the orientation of the subassembly 1402 with respect to the skull M so that the insertion depth of each screw 1440 into the skull M is correspondingly set. Thus, it is not necessary to carefully control the driven depth of the screws 1440 to avoid misaligning or cocking the base portion 1110 with respect to the skull M. Each of the screws 1440 can be driven to the depth appropriate to achieve an appropriate interlock.

The pins 1430 provide additional points of support between the trajectory guide frame 1100 and the skull M. In some embodiments, the pins 1430 are spaced a greater distance apart than the screws 1440 so that the mounting device 1410 can provide stabilizer extensions or outriggers to better resist rotation and cocking of the trajectory guide frame 1100.

By spacing the trajectory guide frame 1100 off of the scalp N, the mounting device 1410 can also facilitate access to the knobs 1166A, 1167A (FIG. 9) for manipulation.

According to some embodiments, the distance D1 (FIG. 1) between the farthest apart pins 1430 is in the range of from about 10 mm to 75 mm.

Advantageously, the assembly 1401 may be suitably mounted on a skull area of substantially any curvature. The assembly 1401 can be mounted on a skull with the screws 1440 extending through the scalp N rather than requiring the scalp N first be removed to allow the base portion 1110 to interface directly with the skull M.

According to some embodiments, the length L1 (FIG. 5) of each pin engagement section 1436 is in the range of from about 3 mm to 20 mm.

According to some embodiments, the length L2 (FIG. 5) of the protruding section 1448 of each screw 1440 between the skull M and the lower surface 1404 is in the range of from about 7 mm to 30 mm. According to some embodiments, the length L3 of the skull embedded section 1446 of each screw 1440 is in the range of from about 2 mm to 10 mm.

Figure 10:
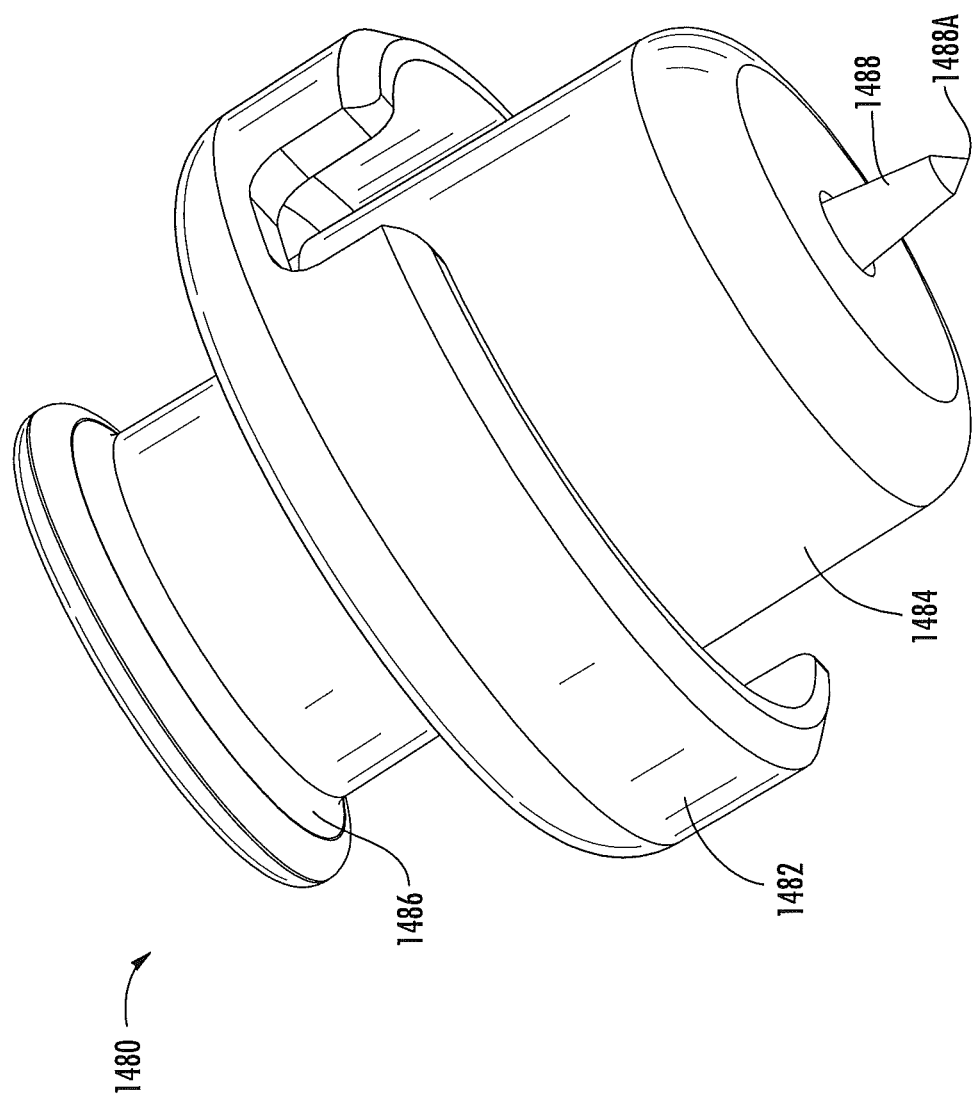
FIG. 10 is a bottom perspective view of a positioning tool according to embodiments of the present invention for use with the trajectory guide frame assembly of FIG. 1.
Figure 11:
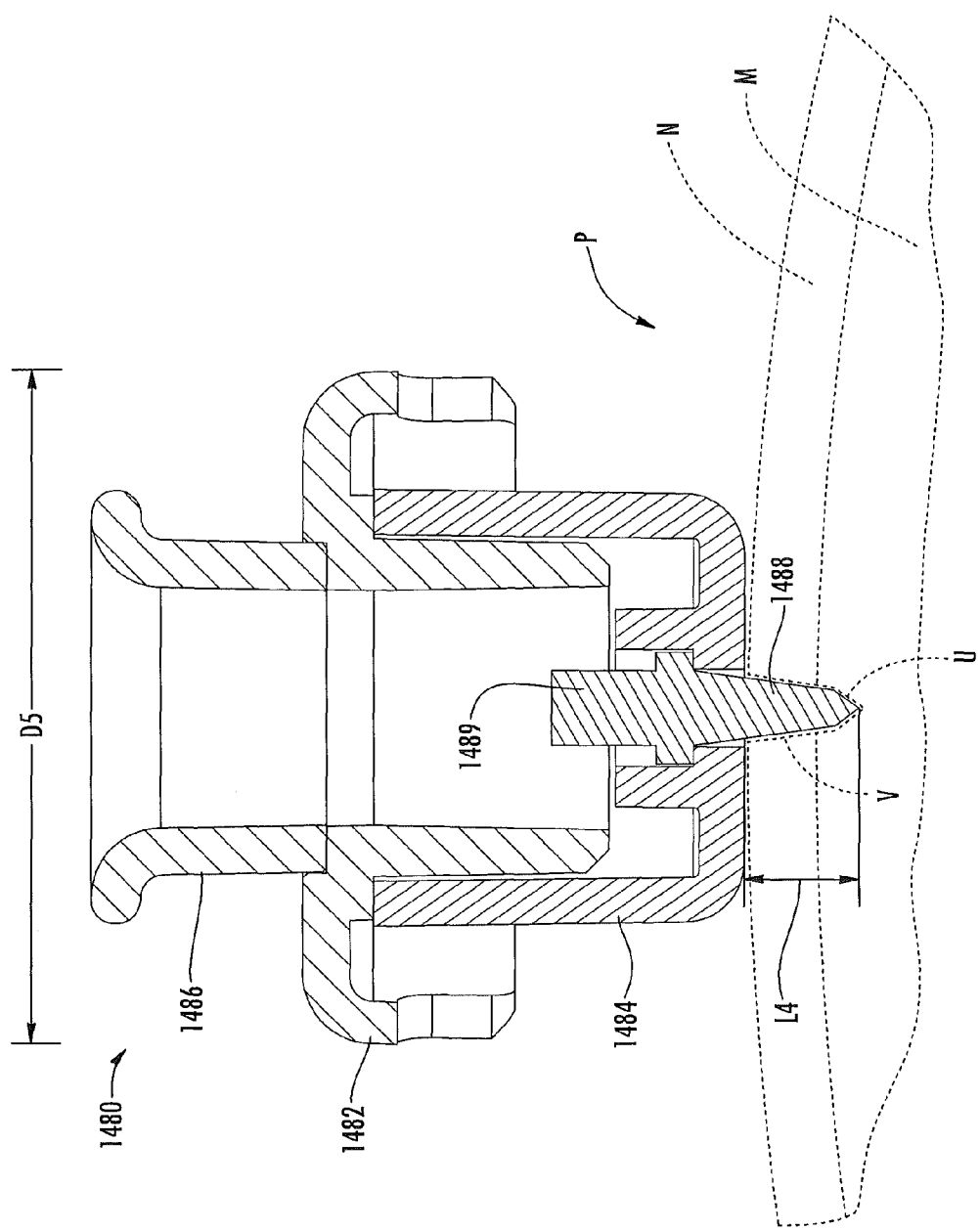
FIG. 11 is a cross-sectional side view of the positioning tool of FIG. 10 mounted on a patient.
Figure 12:
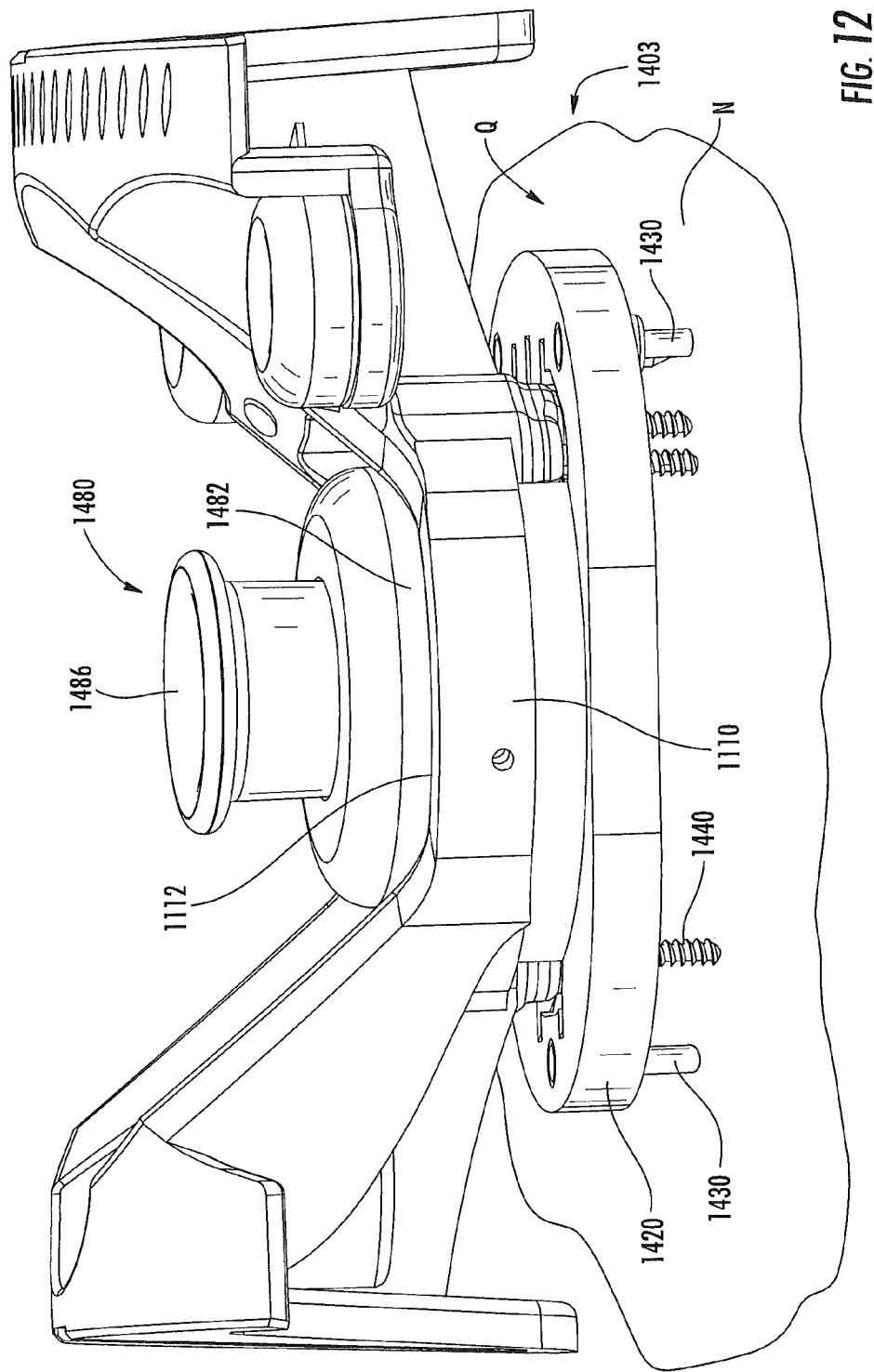
FIG. 12 is a side view of the positioning tool of FIG. 10 and the subassembly of FIG. 2 cooperatively mounted on the patient.

With reference to FIGS. 10-12, a centering or positioning tool 1480 according to embodiments of the present invention is shown therein. The positioning tool 1480 may be used to assist in properly mounting the trajectory guide frame assembly 1401 on a patient P.

The positioning tool 1480 may be formed of any suitable material and, in some embodiments, is formed of an MRI-compatible and/or MRI safe material such as described for forming the mounting member 1420. The positioning tool 1480 may be molded.

The positioning tool 1480 includes a body 1482, an extension 1484 having a reduced diameter as compared to the body 1482, a handle 1486, and an engagement post 1488. The engagement post 1488 may be formed of any suitable material and, in some embodiments, is formed of a material as described above for the pins 1430. The portions 1482, 1484, 1486 may be formed of any suitable material and, in some embodiments, are formed of a material as described above for the mounting member 1420. According to some embodiments and as illustrated, the engagement post 1488 forms a part of a pin 1489 rigidly captured in the portion 1484.

According to some embodiments, the outer diameter D5 of the body 1482 is slightly less than the inner diameter of the access opening 1112 (FIG. 2) of the base portion 1110.

The engagement post 1488 may be conically tapered to a relatively sharp tip 1488A. According to some embodiments, the length L4 (FIG. 11) of the engagement post 1488 extending below the extension 1484 is in the range of from about 6 mm to 7 mm, which corresponds to the typical thickness of a human scalp.

With reference to FIGS. 11 and 12, the positioning tool 1480 may be used as follows in accordance with embodiments of the invention. A puncture V is formed in the scalp N (or other tissue). A blind hole, divot, bore or indentation U may be formed in the skull M (or other boney tissue) of the patient P at a selected location. The puncture V and/or indentation U may be formed using a marking tool as disclosed in U.S. Pat. No. 8,157,828 to Piferi (the disclosure of which is hereby incorporated herein by reference). For example, the marking tool may be inserted through the scalp N to form the puncture V and the indentation U.

The post 1488 of the positioning tool 1480 is inserted into the puncture V as shown in FIG. 11 and may extend into the indentation U, if present. The base 1403 is then placed on the scalp N such that the positioning tool 1480 slides up through the access opening 1112 of the base portion 1110 as shown in FIG. 12. The base 1403 is thereby positively located or centered with respect to the puncture V by the positioning tool 1480 (the post 1488 being seated in the puncture V and/or the indentation U). According to some embodiments, the body 1482 fits snugly in the access opening. The engagement post 1488 is axially concentric with the body 1482 so that the base portion 1110 is thereby centered with respect to the engagement post 1488 and the puncture V and/or indentation U. Alternatively, the positioning tool 1480 can be pre-installed in the base 1403 before mounting the positioning tool 1480 on the scalp N.

The base 1403 may then be pressed against the skull N so that the pins 1430 are driven to puncture or pierce the scalp N and rest against or abut the skull M.

The screws 1440 are then driven (e.g., using a screwdriver) through the base 1403 and into the skull M to secure the base 1430 to the skull M as described above. The screws 1440 may be pre-installed in the screw holes 1114 prior to placing the base 1403 on the scalp N. The screws 1440 are tightened.

The positioning tool 1480 is then removed from the head Q and the base 1403, leaving the base 1403 in place.

With the base 1403 now installed, the yoke 1120 can be installed on the base 1403. If required, a larger incision can be made in the scalp N. The scalp N can be peeled back before or after forming the puncture V or indentation U or mounting the base 1403. A burr hole may be formed through the skull M after mounting the base 1403 on the skull M and before installing the yoke 1120.

In the event the surgeon wants to make a larger incision before securing the base 1403 (e.g., based on the position of the puncture V in the scalp from the marking tool), the surgeon can use the skull indentation U to receive the post 1488 and not the scalp puncture V.

Figure 13:
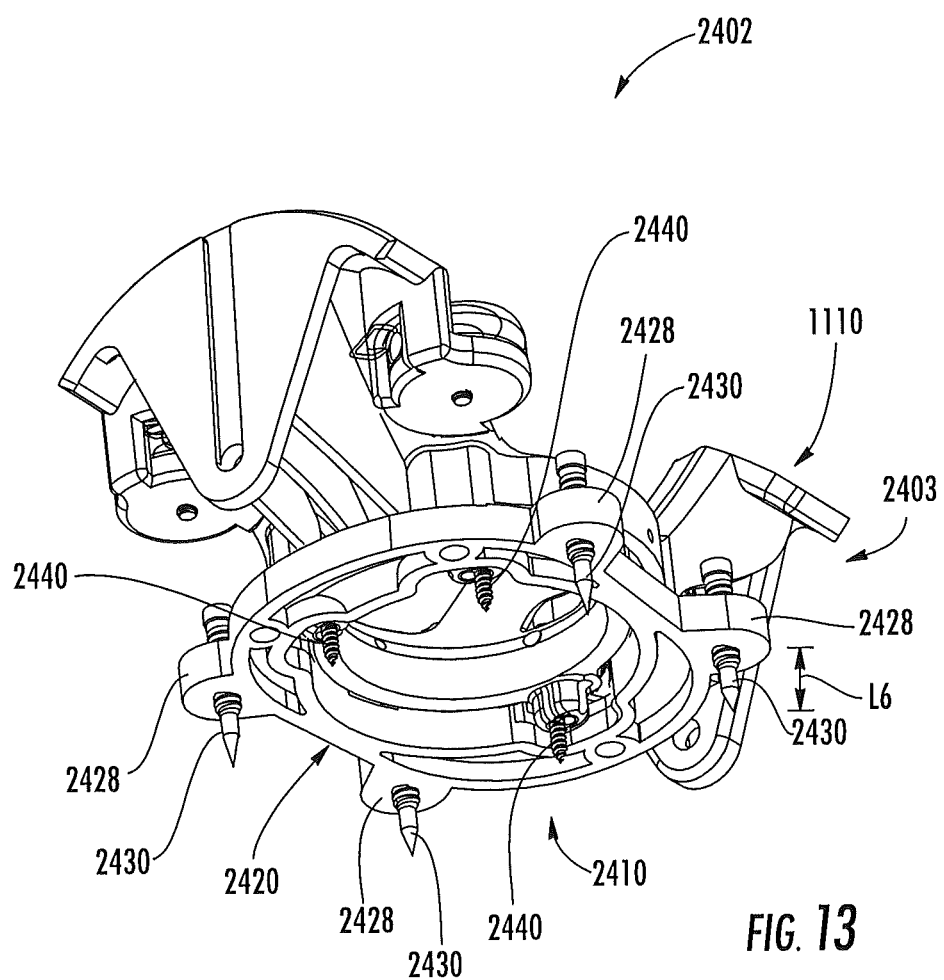
FIG. 13 is a bottom perspective view of a subassembly according to further embodiments of the present invention for mounting a trajectory guide frame on a patient.
Figure 14:
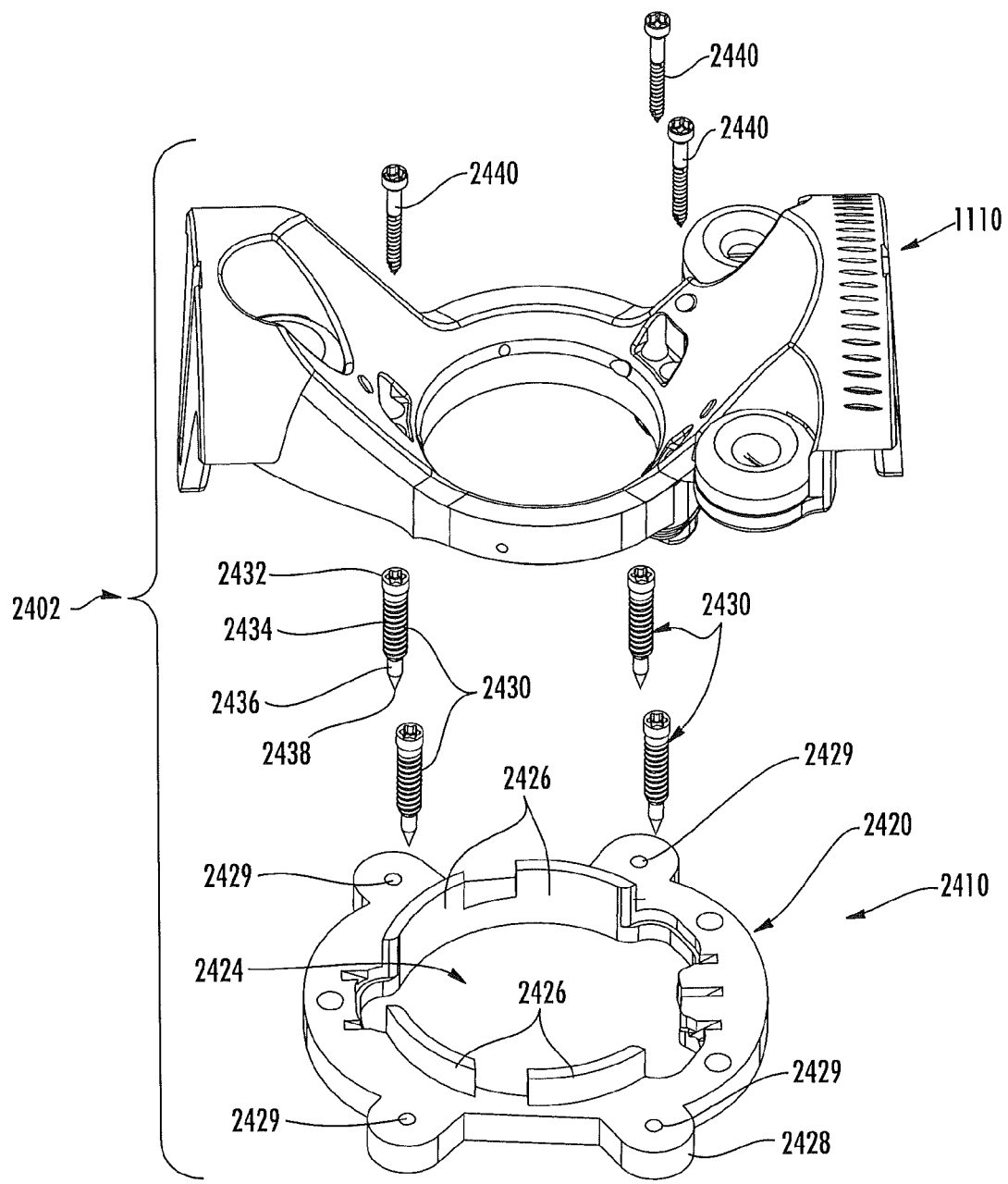
FIG. 14 is an exploded, top perspective view of the subassembly of FIG. 13.

With reference to FIGS. 13 and 14, an alternative subassembly 2402 is shown therein. The subassembly 2402 includes the base portion 1110 and a mounting device 2410 according to further embodiments of the invention. The mounting device 2410 corresponds generally to, is coupled with the base portion 1110 in substantially the same manner as, and is operable in the same manner as the mounting device 1410, except as follows. The subassembly 2402 can be used to mount the trajectory guide frame 1100 on a patient (e.g., on the patient's skull).

The mounting device 2410 includes a mounting member 2420 and four adjustable stabilizer or patient engagement structures 2430. The mounting member 1420 is coupled to the base portion 1110 by a coupling flange or flanges 1426 received in the base coupling slot 1117 and the base flange 1119 received in the mounting device opening 2424.

Each pin 2430 is mounted in a respective threaded bore 2429 formed in a respective integral outrigger tab 2428 of the mounting member 2420. Each pin includes a head 1432, a threaded shaft 2434, a non-threaded spacer or engagement section 2436, and a sharp tip 2438. Each head 2432 is provided with a suitable feature (e.g., a drive socket) configured to receive a driver to forcibly rotate the pin 2430. The shaft 2434 of each pin 2430 is threadedly mounted in its associated threaded bore 2429. As a result, the extension length L6 (FIG. 13) of each pin 2430 can be selectively and independently adjusted, the extension length L6 being the distance from the lower surface 2404 of the mounting device 2420 to the distal tip 2438 of the pin 2430.

The mounting device 2410 and the subassembly 2402 may be used in the same manner as the mounting device 1410 and the subassembly 1402 except as follows in accordance with method embodiments of the invention. The subassembly 2402 includes a base 2403 (formed by the base portion 1110 and the mounting portion 2420). In the case of the mounting device 2410, the mounting screws 1440 are driven into the patient (e.g., into the skull M) to the desired depth to secure the subassembly 2402 to the patient with the pins 2430 raised or backed out so as not to interfere with the mounting screw 1440 installation. One or more of the pins 2430 are then screwed down (increasing their extension lengths L6) onto or into the patient (e.g., onto or into the skull M) to stabilize the subassembly 2402.

It will be appreciated that aspects of the present invention can be used with or incorporated into trajectory guide frames of other types and configurations.

Mounting devices according to embodiments of the invention may be otherwise configured. Other mechanisms may be used to couple the mounting device 1410 or 2410 and the trajectory guide frame 1100.

While a two piece base 1403 or 2403 has been shown and described, according to some embodiments, the structure of the mounting member 1420, 2420 is integrally formed with the base portion 1110. For example, the mounting member 1420 and the base portion 1110 or the mounting member 2420 and the base portion 1110 may be integrally and unitarily molded or assembled (in some embodiments, permanently glued) to form a substantially permanently unitary structure.

While patient engagement structures in the form of separately formed pins 1430 are shown and described, the patient engagement structures may be differently shaped and may be integrally formed with (e.g., integrally molded with) the mounting member 1420 or one-piece base as described above.

The trajectory guide frame systems of the present invention can be provided as a sterile kit (typically as single-use disposable hardware) or in other groups or sub-groups or tools or even individually, typically provided in suitable sterile packaging. The tools can also include a marking grid (e.g., as disclosed in U.S. Published Patent Application No. 2009-00177077 and/or U.S. Published Patent Application No. 2009/00171184). Certain components of the kit may be replaced or omitted depending on the desired procedure. Certain components can be provided in duplicate for bilateral procedures.

Trajectory guide frame systems and mounting devices in accordance with embodiments of the invention may be used to guide and/or place diagnostic or interventional devices and/or therapies to any desired internal region of the body or object using MRI and/or in an MRI scanner or MRI interventional suite. The object can be any object, and may be particularly suitable for animal and/or human subjects. In some embodiments, the guide apparatus is used to place implantable DBS leads for brain stimulation, typically deep brain stimulation. In some embodiments, the guide apparatus can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc. In some embodiments, the interventional tools can be configured to facilitate high resolution imaging via intrabody imaging coils (receive antennas), and/or the interventional tools can be configured to stimulate local tissue, which can facilitate confirmation of proper location by generating a physiologic feedback (observed physical reaction or via fMRI).

In some embodiments, the trajectory guide frame system and mounting device are used for delivering bions, stem cells or other target cells to site-specific regions in the body, such as neurological target and the like. In some embodiments, the guide apparatus is used to introduce stem cells and/or other cardio-rebuilding cells or products into cardiac tissue, such as a heart wall via a minimally invasive MRI-guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Generally stated, some embodiments of the invention are directed to MRI interventional procedures including locally placing interventional tools or therapies in vivo to site-specific regions using an MRI system. The interventional tools can be used to define an MRI-guided trajectory or access path to an in vivo treatment site.

In some embodiments, MRI can be used to visualize (and/or locate) a therapeutic region of interest inside the brain or other body locations, and to visualize (and/or locate) an interventional tool or tools that will be used to deliver therapy and/or to place a chronically implanted device that will deliver one or more therapies. Then, using the three-dimensional data produced by the MRI system regarding the location of the therapeutic region of interest and the location of the interventional tool, the system and/or physician can make positional adjustments to the interventional tool so as to align the trajectory of the interventional tool, so that when inserted into the body, the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An MRI-guided interventional system configured for use with a head of a patient, the head having a skull covered by a scalp, the system comprising:
   an interventional device;
   a base configured to be secured to the head of the patient;
   a trajectory guide frame including a targeting cannula, the targeting cannula being mounted on the base, having an elongate guide bore extending axially therethrough, defining a trajectory axis, and being configured to guide placement of the interventional device, wherein the trajectory guide frame is operable to move the targeting cannula relative to the base to position the trajectory axis to a desired intrabody trajectory to guide placement of the interventional device in vivo;
   a plurality of patient engagement structures on the base configured to penetrate the scalp and to space the base apart from the scalp, each of the patient engagement structures having a distal tip adapted to engage the head; and
   a plurality of screws configured to be screwed into the skull to secure the base to the head;
   wherein the system is configured to allow an extension length of at least one of the patient engagement structures to be selectively adjusted such that the distal tip of the patient engagement structure penetrates the scalp but is not screwed into the skull, the extension length being the length of the patient engagement structure extending from the base to the distal tip, whereby the patient engagement structures serve to space the base apart from the skull and stabilize the base on the skull; and
   wherein each of the patient engagement structures includes a pin including a non-threaded spacer section extending to the distal tip.

2. The MRI-guided interventional system of claim 1 wherein:
   the base includes a base portion and a mounting member;
   the targeting cannula is mounted on the base portion; and
   the mounting member is configured to be coupled to the base portion between the head and the base portion.

3. The MRI-guided interventional system of claim 2 wherein:
   the mounting member includes a plurality of bores;
   the plurality of patient engagement structures includes a plurality of pins each mounted in a respective one of the bores; and
   the base portion includes a plurality of screw holes and each of the screws extends through a respective one of the screw holes.

4. The MRI-guided interventional system of claim 1 wherein the plurality of patient engagement structures each have a sharp tip configured to pierce through the scalp.

5. The MRI-guided interventional system of claim 1 wherein the plurality of patient engagement structures includes at least three patient engagement structures.

6. A method for mounting an MRI-guided interventional system on a patient, the method comprising:
   providing an MRI-guided interventional system configured for use with a head of the patient, the head having a skull covered by a scalp, and an interventional device and including:
      a base configured to be secured to the head of the patient;
      a trajectory guide frame including a targeting cannula, the targeting cannula being mounted on the base, having an elongate guide bore extending axially therethrough, defining a trajectory axis, and being configured to guide placement of the interventional device, wherein the trajectory guide frame is operable to move the targeting cannula relative to the base to position the trajectory axis to a desired intrabody trajectory to guide placement of the interventional device in vivo;
      a plurality of patient engagement structures on the base, each of the patient engagement structures having a distal tip adapted to engage the head; and
      a plurality of screws configured to secure the base to the head;
   securing the base to the head using the plurality of screws, including screwing the plurality of screws into the skull; thereafter
   selectively adjusting an extension length of at least one of the patient engagement structures such that the distal tip of the patient engagement structure penetrates the scalp but is not screwed into the skull, the extension length being the length of the patient engagement structure extending from the base to the distal tip, whereby the patient engagement structures serve to space the base apart from the skull and stabilize the base on the skull; and thereafter
   with the screws screwed into the skull and the patient engagement structures penetrating the scalp but not screwed into the skull, inserting the interventional device through the guide bore and into the head of the patient in vivo.

7. The method of claim 6 wherein the step of securing the base to the head using the plurality of screws includes driving the screws through the scalp and into the skull.

8. The method of claim 6 wherein:
   the base includes a base portion and a mounting member; and
   the method includes:
      coupling the mounting member between the head and the base portion; and
      mounting the targeting cannula on the base portion.

9. The method of claim 6 wherein the plurality of patient engagement structures include a plurality of pins.

10. The method of claim 6 wherein the plurality of patient engagement structures each have a sharp tip configured to pierce through the scalp.

11. The method of claim 6 wherein the plurality of patient engagement structures includes at least three patient engagement structures.

12. The method of claim 6 including placing a positioning tool on the head in a selected location, wherein mounting the base on the head includes mounting the base over the positioning tool to positively locate the base with respect to the selected location.

13. The method of claim 12 including pre-forming a puncture in the head, wherein the puncture is at the selected location.

14. The method of claim 6 including mounting the trajectory guide frame on the base after securing the base to the head using the plurality of screws.

15. The method of claim 14 including forming a burr hole in the head before or after securing the base to the head.

16. The method of claim 15 including using the trajectory guide frame to guide a drill bit to form the burr hole.

* * * * *

UNITED STATES PATENT AND TRADEMARK OFFICE
CERTIFICATE OF CORRECTION

| | | |
|---|---|---|
| PATENT NO. | : 9,192,446 B2 | Page 1 of 1 |
| APPLICATION NO. | : 13/801190 | |
| DATED | : November 24, 2015 | |
| INVENTOR(S) | : Piferi et al. | |

It is certified that error appears in the above-identified patent and that said Letters Patent is hereby corrected as shown below:

In the Specification

Column 8, Line 47: Please correct "height 112 of the gap"
to read -- height H2 of the gap --

Column 8, Line 51: Please correct "the height 112 will"
to read -- the height H2 will --

Signed and Sealed this
Seventh Day of June, 2016

Michelle K. Lee
*Director of the United States Patent and Trademark Office*